US011717142B2

(12) United States Patent
Sitti et al.

(10) Patent No.: US 11,717,142 B2
(45) Date of Patent: Aug. 8, 2023

(54) SIMULTANEOUS CALIBRATION METHOD FOR MAGNETIC LOCALIZATION AND ACTUATION SYSTEMS

(71) Applicant: MAX-PLANCK-GESELLSCHAFT ZUR FÖRDERUNG DER WISSENSCHAFTEN E.V., Munich (DE)

(72) Inventors: Metin Sitti, Stuttgart (DE); Donghoon Son, Daegu (KR); Xiaoguang Dong, Nenjiang (CN)

(73) Assignee: MAX-PLANCK-GESELLSCHAFT ZUR FÖRDERUNG DER WISSENSCHAFTEN E.V, Munich (DE)

( * ) Notice: Subject to any disclaimer, the term of this patent is extended or adjusted under 35 U.S.C. 154(b) by 925 days.

(21) Appl. No.: 16/696,605

(22) Filed: Nov. 26, 2019

(65) Prior Publication Data

US 2020/0196844 A1 Jun. 25, 2020

(30) Foreign Application Priority Data

Dec. 10, 2018 (EP) ..................................... 18211302

(51) Int. Cl.
*A61B 1/04* (2006.01)
*A61B 34/00* (2016.01)
*A61B 1/00* (2006.01)
*G01R 33/00* (2006.01)
(Continued)

(52) U.S. Cl.
CPC ........ *A61B 1/041* (2013.01); *A61B 1/000096* (2022.02); *A61B 1/00158* (2013.01);
(Continued)

(58) Field of Classification Search
CPC combination set(s) only.
See application file for complete search history.

(56) References Cited

U.S. PATENT DOCUMENTS

2010/0234685 A1* 9/2010 Juloski .................. A61B 1/041
600/117
2011/0046443 A1 2/2011 Hironao et al.
(Continued)

FOREIGN PATENT DOCUMENTS

DE 102007051860 A1 7/2009
EP 2105085 A1 3/2009

OTHER PUBLICATIONS

Official Communication from the European Patent Office for related European Patent Application No. 18211302.7 dated May 31, 2019; 3 pages.
(Continued)

*Primary Examiner* — Alvaro E Fortich
(74) *Attorney, Agent, or Firm* — Dickinson Wright PLLC

(57) ABSTRACT

The invention relates to a method of simultaneously calibrating magnetic actuation and sensing systems for a workspace, wherein the actuation system comprises a plurality of magnetic actuators and the sensing system comprises a plurality of magnetic sensors, wherein all the measured data is fed into a calibration model, wherein the calibration model is based on a sensor measurement model and a magnetic actuation model, and wherein a solution of the model parameters is found via a numerical solver order to calibrate both the actuation and sensing systems at the same time.

19 Claims, 8 Drawing Sheets

Figure 1:
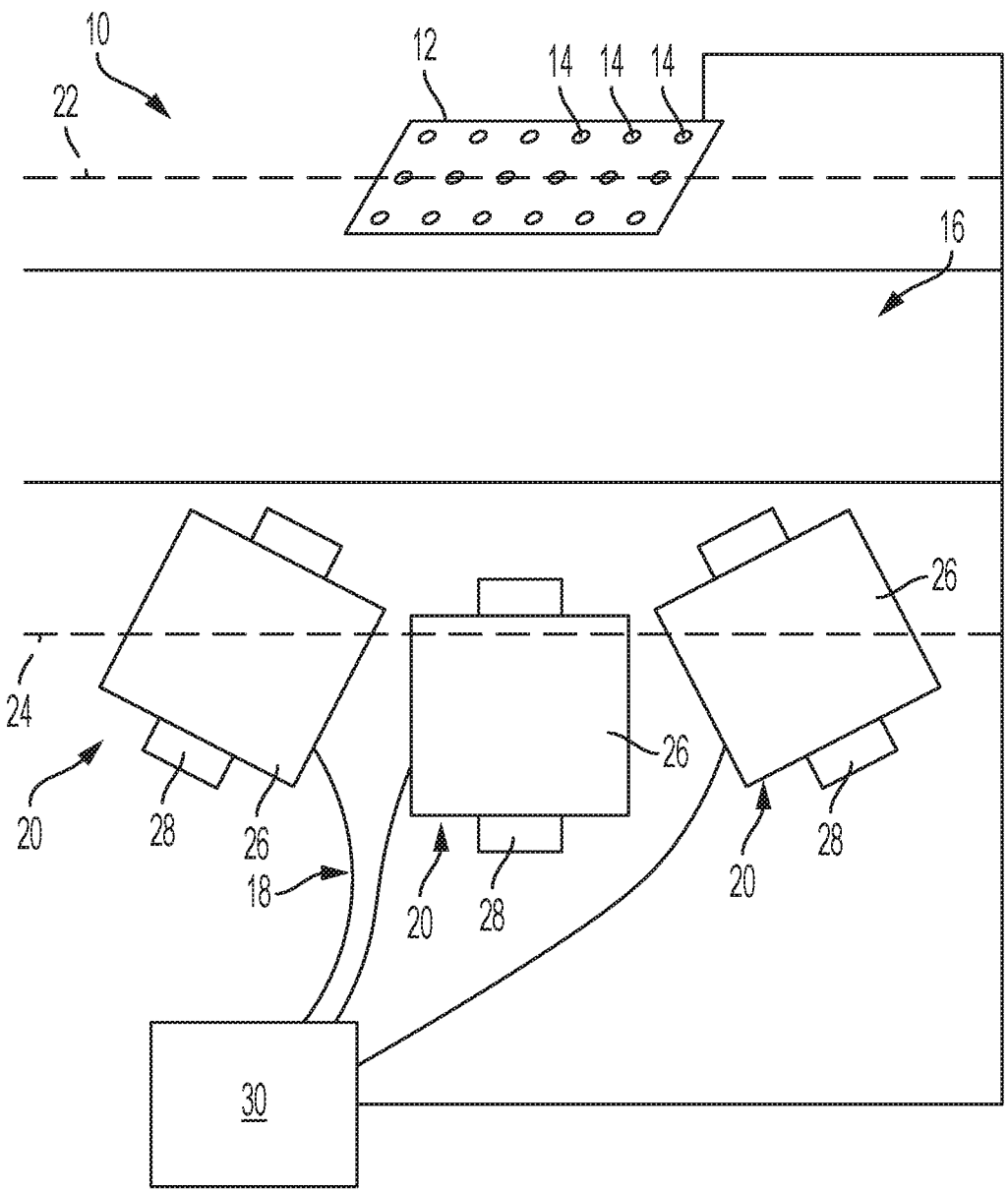

(51) Int. Cl.
*A61B 5/06* (2006.01)
*G01C 25/00* (2006.01)
*A61B 34/20* (2016.01)
*A61B 17/00* (2006.01)
*A61B 34/30* (2016.01)

(52) U.S. Cl.
CPC ............. *A61B 5/062* (2013.01); *A61B 34/20* (2016.02); *A61B 34/73* (2016.02); *G01C 25/00* (2013.01); *G01R 33/0017* (2013.01); *G01R 33/0035* (2013.01); *A61B 2017/00725* (2013.01); *A61B 2034/2051* (2016.02); *A61B 2034/303* (2016.02)

(56) References Cited

U.S. PATENT DOCUMENTS

| | | | |
|---|---|---|---|
| 2013/0245834 A1* | 9/2013 | Laxhuber ............ | A61C 1/0023 700/275 |
| 2016/0086080 A1* | 3/2016 | Foong ................... | A61B 5/062 706/25 |
| 2017/0209072 A1* | 7/2017 | Oren ..................... | G01R 33/02 |
| 2017/0299662 A1* | 10/2017 | Nagasaka ............ | G01R 33/035 |

OTHER PUBLICATIONS

"A Simultaneous Calibration Method for Magnetic robot Localization and Actuation Systems" from Donghoon Son, Student Member, IEEE, Xiaoguang Dong, Student Member, IEEE, and Metin Sitti, Fellow, IEEE, pp. 1-10.

"Model-Based Calibration for Magnetic Manipulation" from Andrew J. Petruska, Janis Edelmann, and Bradley J. Nelson; IEEE Transactionis on Magnetics, IEEE Service Center, New York, NY, US, vol. 53, No. 7, Jul. 1, 2017 (Jul. 1, 2017), pp. 1-6, XP011653223, ISSN: 0018-9464, DOI: 10.1109/TMAG.2017.2653080 [retrieved on Jun. 19, 2017] *section "III. Calibration"*.

* cited by examiner

TABLE I
PARAMETRIZATION

| $i$-th Sensor Parameter ($1 \leq i \leq N$) | Symbol and Space |
|---|---|
| Position vector | $r_i \in R^3$ |
| Non-orthogonal sensitivity matrix with rotation | $G_i \in R^{3 \times 3}$ |
| Quadratic sensitivity matrix | $^XH_i, {}^YH_i, {}^ZH_i \in SR^{3 \times 3}$ |
| $j$-th Actuator Parameter ($1 \leq j \leq M$) | |
| Position vector | $r_j \in R^3$ |
| Magnetic moment vector | $m_j \in R^3$ |
| $k$-th Measurement Values ($1 \leq k \leq L$) | |
| $i$-th magnetic sensor reading | $v_{ik} \in R^{3N}$ |
| $j$-th current sensor reading | $I_{jk} \in R^M$ |

*R: Euclidean space; $SR^{n \times n}$: n-dimensional systemic matrix N, M, L: The total number of sensors, actuators, and measurements

FIG. 2

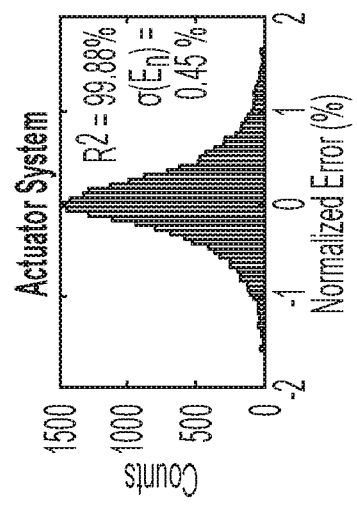
FIG. 4A
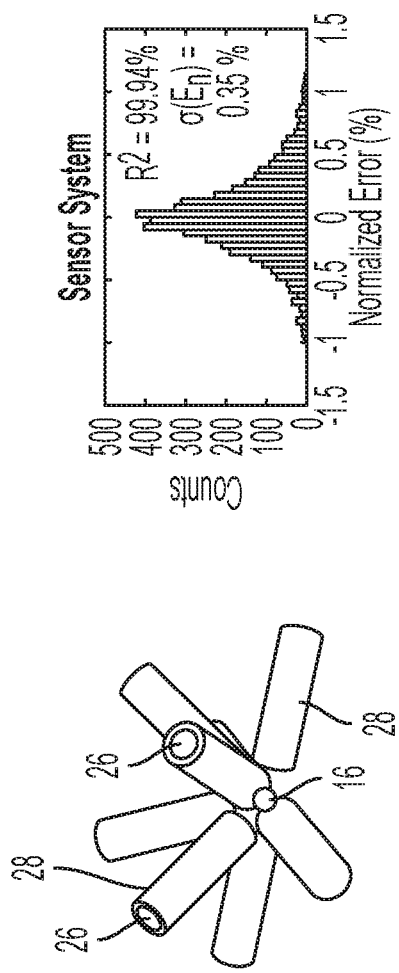
FIG. 4C
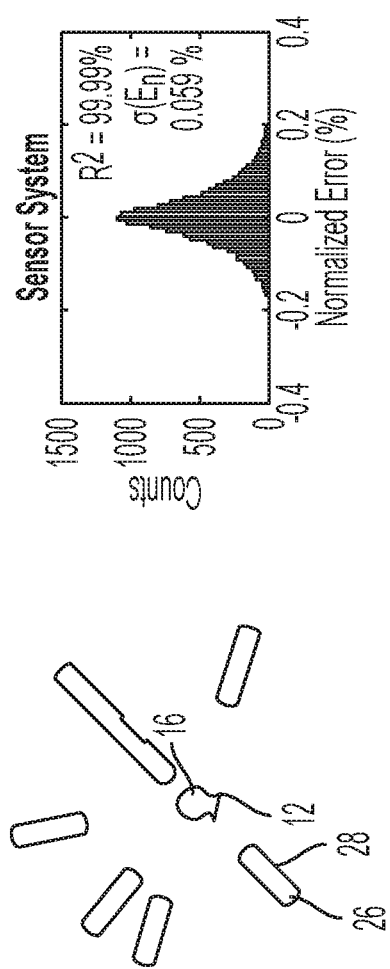
FIG. 4E
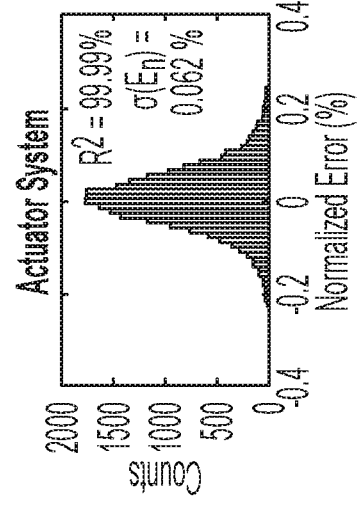
FIG. 4B
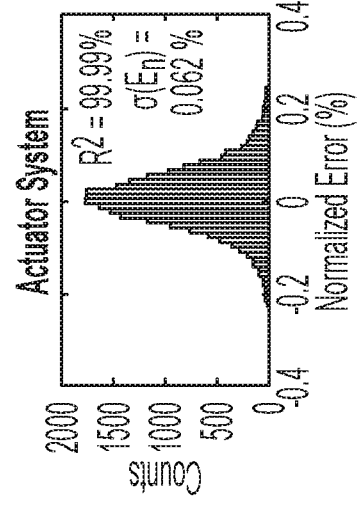
FIG. 4D
FIG. 4F

TABLE II
SPECIFICATION OF THE LOCALIZATION AND ACTUATION SETUP

|  | Value |
|---|---|
| Magnetic sensor | LIS3MDL, STMicroelectronics |
| - Nodal distance | 30 mm |
| - Sensitivity | 17.11 bit/μT (digitial) |
| - RMS Noise | 0.32 μT (x-, y-axis), 0.41 μT (z-axis) |
| Current sensor | Current sensor of ESCON 70/10, Maxon Motor |
| - Sensitivity | 1 V/A |
| - Noise | 0.735 mA |
| Soft-iron core | Permenorm 5000 H2, VACUUMSCHMELZE |
| - Material | Ni-Fe |
| - Dimension | $\Phi 36 \times 160$ mm$^3$ |
| Copper-wire coil | ENOFLEX-180 ($\Phi 1.18$ mm), HELCA Metal |
| - Dimension | ($\Phi 40$(in)-100(out))$\times 80$ mm, 1500 turns |
| Refrence magnet | NdFeB N42 |
| - Dimension | $\Phi 10 \times 10$ mm$^3$ |
| - Magnetic moment | 0.836 A·m$^2$ |
| Current drive (ESCON 70/10, Maxon Motor) | |

FIG. 5

TABLE III
INITIAL PARAMETERS AND TOLERANCES

| Parameters | Initial Value and Tolerance |
|---|---|
| $r_j$ | $r_{j,ideal}{}^* \pm 40$ mm |
| $G_i$ | $58 \times I \pm 5.8$ nT/bit |
| $H_i$ | $O \pm 5.8$ nT/bit$^2$ |
| $m_j$ | $m_{j,ideal}{}^* \pm 40$ A·m$^2$/A |

$I$ and $O$ are an identity matrix and a zero matrix in $R^{3 \times 3}$, respectively
* $r_{j,ideal}$, $m_{j,ideal}$ are designed position values of each sensor and actuator.

FIG. 6

SIMULTANEOUS CALIBRATION METHOD FOR MAGNETIC LOCALIZATION AND ACTUATION SYSTEMS

The invention relates to a method of simultaneously calibrating magnetic actuation and sensing systems for a workspace, wherein the actuation system comprises a plurality of magnetic actuators and the sensing system comprises a plurality of magnetic sensors.

Magnetically actuated capsule endoscopes (MACEs) belong to a promising medical field of technology for minimally invasive diagnosis in the gastrointestinal (GI) tract. MACE localization and actuation is already known. Among the various localization methods, magnetic localization techniques using an external magnetic sensor array are more promising for practical applications because they minimize the volume, energy consumption and complexity of the necessary capsule components. For the actuation of a capsule, electromagnet-based actuation is safer than permanent-magnet-based actuation.

The combination of magnetic localization and actuation techniques is beneficial because the remotely actuated device only needs to include a singlet magnet. Especially important for robots with size limitations, such as a robotic capsule endoscope, this approach reduces the required volume in comparison to devices with additional tracking tools. The saved volume could be utilized for other critical functions, such as high quality video or a high capacity battery, which may improve the quality of a diagnosis.

The combination of both systems can have various configurations and requires a high standard of calibration. This is because the sensing and actuation systems share the magnetic field, where the magnetic fields from the robot and the actuation systems are superimposed together. In such a case, the decoupling of the robot's magnetic field from the actuator's field relies on a precisely calibrated parametric magnetic model.

Moreover, in time the gain values (parameter values) of the sensors and the actuators can drift and hence such actuators and sensors require calibration within certain periods of time, such as weeks. Thus, particularly for medical imaging and scanning devices the down time during calibration has to be reduced.

Inaccurate actuation and sensing models could lead to a false position and orientation estimation of the robot. This could cause an error or a failure of the control for the magnetic robot.

A known way to calibrate a combined magnetic actuation and sensing system is to independently calibrate the actuation system and the sensing system. For the calibration of the magnetic sensor system, the position, orientation and gain of each sensor can be calibrated either individually or simultaneously.

Also methods to calibrate actuation systems, for example for multi-core electromagnetic actuation systems, are known. One such method uses a numerical optimization with a multipole magnetic field model. Measurement data are gathered using a pre-calibrated Gauss meter, when the actuation system generates the magnetic field.

A disadvantage of these two methods for calibration is that they cannot be combined and thus executed simultaneously. A simultaneous calibration method can be advantageous over separate calibration methods in several aspects, such as improved accuracy and speed of the calibration process.

It is therefore an object of the invention to provide a method and a system in which the calibration process can be carried out with an improved accuracy and speed of the calibration process.

This object is satisfied by a method of simultaneously calibrating magnetic actuation and sensing systems for a workspace and a magnetic actuation and sensing system with the features of the respective independent claims.

According to the invention the method comprises the following steps:
- generating a plurality of arbitrary magnetic fields at the workspace by applying a plurality of electric currents at the magnetic actuators;
- measuring each magnetic field with the sensing system in the workspace and measuring each respective electric current with a current sensor;
- measuring a magnetic field of a random known sample magnet with the sensing system at an arbitrary position and orientation in the workspace level; and
- feeding all the measured data into a calibration model, wherein the calibration model is based on a sensor measurement model and a magnetic actuation model, and finding a solution of the model parameters via a numerical solver in order to calibrate both the actuation and sensing systems at the same time.

In the simultaneous calibration method, uncalibrated sensors and actuators work as respective calibration sources. Although the data of the system is inaccurate before the calibration, all the data for the sensing and actuation systems is calibrated simultaneously by the property of the calibration model. It is assumed that the electric current sensors are pre-calibrated before the calibration and the positions of the magnetic sensors are known.

According to the invention the method is basically composed of three steps. First the magnetic actuators generate a number of random magnetic fields creating a respective measurement instance. For each measurement instance, the magnetic field is measured by the workspace by magnetic sensors while the electric currents are measured by a current sensor present at each actuator. Since it is known that the electric current is proportional to the voltage applied, one could also imagine measuring the respective voltage instead of the electric current.

The workspace describes an area in the system which can be composed of one or more levels spanning a volume. The workspace is located as close as possible to the sensing and actuating system, preferably between the sensors and the actuators, but is still spaced far enough from the sensing and actuating systems in order to provide enough room for an object or a patient to be placed in the workspace.

In a second step, the magnetic field of a known sample magnet is measured by the sensing system. The sample magnet is placed inside the workspace with an arbitrary position and orientation. The sample magnet can be a permanent magnet in order to be used as a physical reference by measuring the magnetic field of the permanent magnet inside the workspace.

In a third step, all the measurement data is fed into the calibration model. According to the invention the calibration model comprises a combined sensor measurement model and magnetic actuation model with calibration model parameters that are used to calibrate both the actuation and sensing systems at the same time by finding a solution to the calibration model parameters via a numerical solver. Unlike the prior art there is no need to calibrate the sensing and actuation systems independently. This reduces the amount of calculation time required for the calibration and also ensures that the same magnetic field is used to calibrate the actuators and the sensors so that these are calibrated to the same corresponding magnetic field.

The simultaneous calibration has several advantages. First, the simultaneous calibration method enables automated self-calibration of the system, i.e. the system is adapted to be calibrated without human input. This significantly improves the accuracy and the speed of the calibration process. This is because the large data set is provided by the automated process in a relatively short time, without errors from manual operations. The whole procedure can be done in fifteen minutes, preferably five minutes or less with a good precision in a real system. Second, the simultaneous calibration method allows a coordination calibration between the sensing system and the actuation system, which is not possible with separate calibration methods. Third, the simultaneous automatic calibration method enables system parameter updates for both long-term correctness and flexible reconfiguration for specific tasks.

According to a first aspect of the present invention the actuation and sensing systems each comprise an actuation system level and a sensing system level, respectively, wherein the workspace is sandwiched in between the actuation system level and the sensing system level. As mentioned earlier the workspace can comprise one or more levels as long as all the present levels are sandwiched between the actuation system level and the sensing system level. In real applications the workspace might have dimensions which allow a patient to be positioned in the workspace, namely between the actuation system level and the sensing system level.

According to another aspect of the invention the magnetic actuators comprise electromagnets. A typical electromagnet has a coil and a core, and their axes are aligned together. For example a solenoidal shape of the electromagnets can be used.

Another aspect of the invention relates to the feature that the magnetic sensors can either be mono-axial or multi-axial, particularly triaxial, sensors. Multi-axial sensors are harder to calibrate but can contribute to a more accurate calibration of the systems.

Preferably each of the plurality of generated magnetic fields is non-uniform solenoidal shape throughout the workspace. Preferably the magnetic fields vary in at least one of time and magnitude throughout the plurality of sensors, preferably both in time and in space. A local dependence as well as a temporal dependence result in the fact that each sensor of the plurality of magnetic sensors measures a different value. Actuation systems using non-uniform solenoidal magnetic fields, such as the OctoMag- or MiniMag- systems, are well known, and can be categorized as applicable systems for the invention.

It is preferred if the calibration model comprises a parameter set, which includes sensor parameters and actuator parameters, wherein the sensor parameters comprise parameters for position, orientation, axis distortion, axes distortion and gain of each sensor, and wherein the actuator parameters comprise parameters for position, orientation and magnetic moment of each actuator. Therefore, the proposed method involves a large set of parameters in order to achieve an accurate calibration for the actuating and sensing systems.

For a general sensor calibration each sensor is regarded as having a non-linear response and a cross-coupling effect among the axes. The non-linearity is attributed by hard-iron or soft-iron effect from ferrous material. Distortion of axes can be attributed by fabrication errors form the manufacturing process or thermal stress from the soldering process. In a case of extremely sensitive triaxial magnetometers, a transverse field effect (TFE) can become an additional source for the non-linearity and cross-coupling effects.

Furthermore, the sensor parameters can be determined via a 3-D polynomial model which can easily be expanded by increasing the order of polynomials with expense of computation.

A typical magnetic actuator, such as an electromagnet, has a coil and a core, and their axes are aligned together. In such a case, the orientation and the magnitude of the magnetic moment of the electromagnet can be combined into a 3-D vector.

According to an aspect of the invention the sensor measurement model includes a measurement of each generated magnetic field according to $$\overline{b}_{ik}(p_{si}, v_{ik}) \propto G_i v_{ik} + \begin{bmatrix} v_{ik}^T H_{x,i} v_{ik} \\ v_{ik}^T H_{y,i} v_{ik} \\ v_{ik}^T H_{z,i} v_{ik} \end{bmatrix}, \text{preferably} \quad (1)$$

$$\overline{b}_{ik}(p_{si}, v_{ik}) = G_i v_{ik} + \begin{bmatrix} v_{ik}^T H_{x,i} v_{ik} \\ v_{ik}^T H_{y,i} v_{ik} \\ v_{ik}^T H_{z,i} v_{ik} \end{bmatrix},$$

wherein $p_{s,i}$ is an array of parameters for $G_i$, $H_{x,i}$, $H_{y,i}$, and $H_{z,i}$, and wherein $H_{x,i}$, $H_{y,i}$ and $H_{z,i}$ are symmetric 3×3 matrices which involve rotations and quadratic terms together, $G_i$, is a linear mapping which represents effects of scaling, rotation and shear, and $v_{ik}$ is the magnetic senor reading.

It is assumed that a single sensor reads the magnetic flux density, or the B-field, through the voltage difference across the ends of a magneto-sensitive resistor. Furthermore, it is assumed that the sensor is non-linear, the axes of which are skewed and rotated, and the gains are different from factory specifications. In order to get to the above equation a quadratic model is used to describe the recovered B-field on the i-th sensor at the k-th measurement.

It is another aspect of the invention that the recovered B-field values are expressed in a stacked matrix form as $$\overline{\nabla}_s(p_s, v) \propto \begin{bmatrix} \overline{b}_{11}(p_{s,1}, v_{11}) & \cdots & \overline{b}_{1L}(p_{s,1}, v_{1L}) \\ \vdots & \ddots & \vdots \\ \overline{b}_{N1}(p_{s,N}, v_{N1}) & \cdots & \overline{b}_{NL}(p_{s,N}, v_{NL}) \end{bmatrix}, \text{preferably} \quad (2)$$

$$\overline{\nabla}_s(p_s, v) = \begin{bmatrix} \overline{b}_{11}(p_{s,1}, v_{11}) & \cdots & \overline{b}_{1L}(p_{s,1}, v_{1L}) \\ \vdots & \ddots & \vdots \\ \overline{b}_{N1}(p_{s,N}, v_{N1}) & \cdots & \overline{b}_{NL}(p_{s,N}, v_{NL}) \end{bmatrix},$$

and wherein $p_s$ and $v$ are stacked vectors for all $p_{s,i}$ and $v_{ik}$, respectively. As each sensor of the plurality of sensors has multiple measurements, it is convenient to express the recovered B-field values from the whole measurements as mentioned above.

Preferably the magnetic actuation model is based on a dipole model, where a dipole magnetic field on the i-th sensor from the j-th actuator at the k-th measurement is expressed as $$b_{ij,k} \propto B_{ij} m_j I_{jk}; B_{ij} \frac{\mu_0}{4\pi \|r_{ij}\|^3}(3\hat{r}_{ij}\hat{r}_{ij}^T - \mathbb{1}), r_{ij} \propto r_i - r_j, \text{preferably} \quad (3)$$

-continued $$b_{ij,k} = B_{ij} m_j I_{jk}; \quad B_{ij} \equiv \frac{\mu_0}{4\pi \|r_{ij}\|^3} (3\hat{r}_{ij}\hat{r}_{ij}^T - \mathbb{I}), \quad r_{ij} \equiv r_i - r_j,$$

where $b_{ij,k}$ is a magnetic field vector, $B_{ij}$ is a 3×3 matrix which only depends on the displacement vector $r_{ij}$, $\mathbb{I}$ is the identity matrix and $\mu_0$ is the permeability of free space. Here [|$]$ $$[|$]$ $\hat{AX}$[|]$$$ m (hat) is an operator to make a vector a as a unit vector with the same orientation. Also quadrupole models or higher order magnetic spherical expansion models could be possible.

According to one aspect of the invention the magnetic fields at multiple measurement points are expressed as $b_k \propto \mathbb{B} \mathbb{M} i_k$, preferably $b_k = \mathbb{B} \mathbb{M} i_k$ (4), where $$\mathbb{B} \propto \begin{bmatrix} B_{11} & \cdots & B_{1M} \\ \vdots & \ddots & \vdots \\ B_{N1} & \cdots & B_{NM} \end{bmatrix}, \mathbb{M} \propto \begin{bmatrix} m_1 & \cdots & 0 \\ \vdots & \ddots & \vdots \\ 0 & \cdots & m_M \end{bmatrix}, \text{ preferably } \mathbb{B} = \begin{bmatrix} B_{11} & \cdots & B_{1M} \\ \vdots & \ddots & \vdots \\ B_{N1} & \cdots & B_{NM} \end{bmatrix} \text{ and } \mathbb{M} = \begin{bmatrix} m_1 & \cdots & 0 \\ \vdots & \ddots & \vdots \\ 0 & \cdots & m_M \end{bmatrix},$$
(4)

$b_k$ are modelled magnetic fields on all the sensors, $\mathbb{B}$ is an actuation matrix mapping magnetic moments to the magnetic field on each sensor, $\mathbb{M}$ is a magnetic moment package for the actuators and $i_k$ is a measured electric current for all the actuators in a stacked form at the k-th measurement.

According to another aspect of the invention the B-field values are expressed as a stacked matrix form as $\mathbb{V}_a(p_a, i) \propto [b_1 \ldots b_L] \propto \mathbb{B} \mathbb{M} [i_1 \ldots i_L] \propto \mathbb{B} \mathbb{M} \mathbb{J}$, preferably as
$$\mathbb{V}_a(p_a, i) = [b_1 \ldots b_L] = \mathbb{B} \mathbb{M} [i_1 \ldots i_L] = \mathbb{B} \mathbb{M} \mathbb{J} \quad (5),$$

where $p_a$ is a vector including all actuation parameters, especially the actuator parameters according to claim 6, i is a stacked vector for all $i_k$, and $\mathbb{J}$ is a stacked matrix for all current measurements. It is simply convenient to express the B-field values in to a stacked matrix.

It is preferred if the calibration model comprises a cost function which minimizes errors between the B-field values, especially the B-field values given by the sensor measurement model and the magnetic actuation model, wherein the cost function is formulated as $$\underset{p_s, p_a}{\text{minimize}} \| \mathbb{V}_s(p_s, v) - \mathbb{V}_a(p_a, i) \|_F^2 \quad (6)$$

$$\text{subject to } p_{s,lb} \leq p_s \leq p_{s,ub}$$
$$p_{a,lb} \leq p_a \leq p_{a,ub}$$
$$g(p_s) = 0,$$

where $\|\bullet\|_F$ is the Frobenius norm, $p_s$ are sensor parameters $p_{s,lb}$ and $p_{s,ub}$ are sensor parameters' lower and upper boundaries, respectively, $p_a$ are actuator parameters and $p_{a,lb}$ and $p_{a,up}$ are actuator parameters' lower and upper boundaries, respectively. The upper and lower boundaries for the sensor parameter and actuator parameter can each lie within a 10% estimate.

Advantageously a temporary magnetic scale is added to the calibration model, which is derived from $$\text{mean}\left(\frac{\|G_i\|_F^2}{3}\right) - g^2 = 0, \quad (8)$$

where g is a gain value of the sensors. The temporary magnetic scale can either be fixed by constraining the sensor gain or the magnetic moment of the actuator to a certain number.

It is preferred if the calibration model comprises an optimization, which is formulated as $$\underset{\alpha, r, \hat{n}_r}{\text{minimize}} \| \alpha \mathbb{V}(p_s, v_r) - [B_{ir} \ldots B_{Nr}]^T \hat{n}_r m \|_2^2 \quad (9)$$

where $\alpha$ is a magnetic scale correction factor, $v_r$ is the magnetic field measurement data when the sample magnet is in the workspace level, $B_{ir}$ is formulated using relative positions $r_i$-$r_r$, $r_r$ is the position of the sample magnet, $\hat{n}_r$ is an orientation vector of the sample magnet and m is a known magnetic moment of the sample magnet. By using $\alpha$ from the optimization, the magnetic scales can be reassigned as $$G^*_i = \alpha G_i, H^*_i = \alpha H_i, m^* = \alpha m \quad (10)$$

where the "*" symbol means a corrected value.

The invention further relates to a magnetic actuation and sensing system, comprising a plurality of magnetic actuators and a plurality of magnetic sensors, a respective output of the plurality of magnetic actuators and of the plurality of magnetic sensors being made available at a common evaluation unit, the evaluation unit being configured to simultaneously calibrate the magnetic actuators and the magnetic sensors in accordance with a method of the invention using a calibration model.

According to one aspect of the invention the plurality of magnetic actuators comprises 3 to 25, preferably between 3 and 12, magnetic actuators; and/or wherein the plurality of magnetic sensors comprises between 9 and 256, preferably between 32 and 128 magnetic sensors, preferably wherein the number of magnetic sensor parameters and the number of magnetic actuator parameters are 27N and 6M, respectively, which formulates an inequality which, in the case of a triaxial sensor, can be expressed as 3NL+1≥27N+6M, which results in $$L \geq 9 + \frac{6M - 1}{3N}. \quad (7),$$

where L represents a total number of measurements. This basically means that the total number of equations should be larger than the total number of parameters to solve the optimization problem. Therefore, equation (7) gives a minimum number of measurements which are needed to solve the problem.

Figure 3:
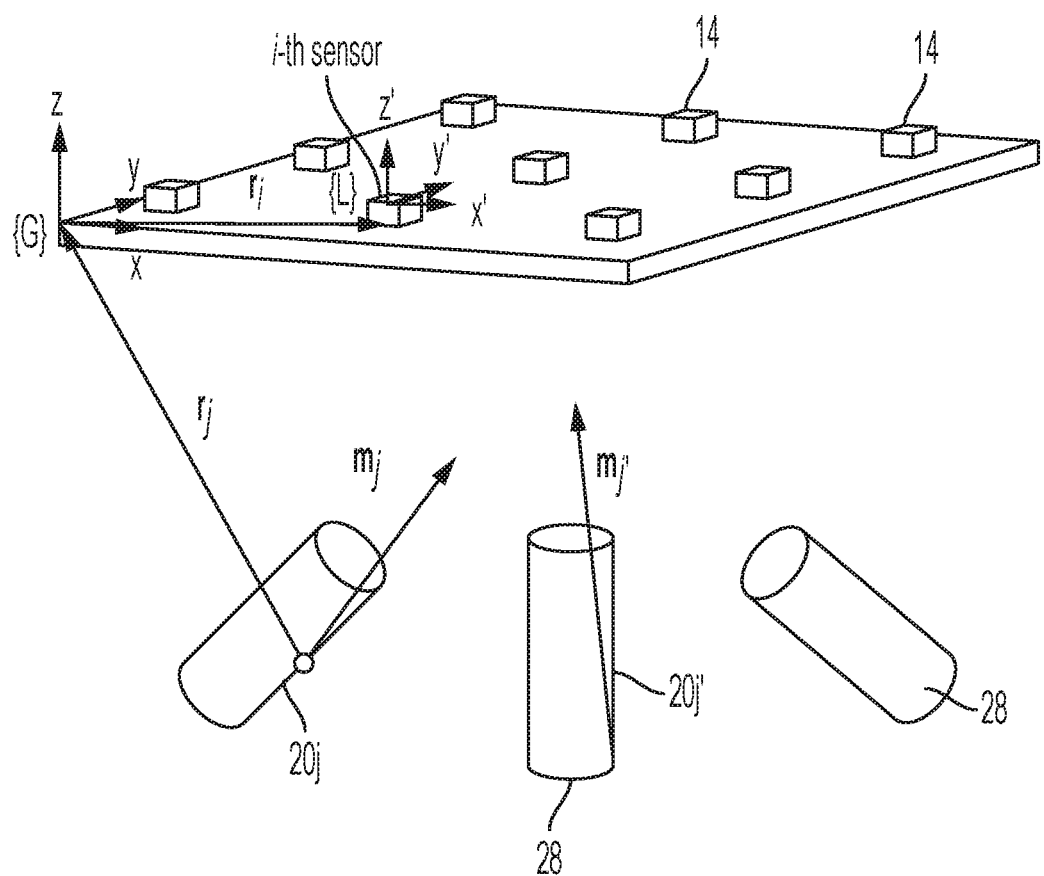
Figure 7A:
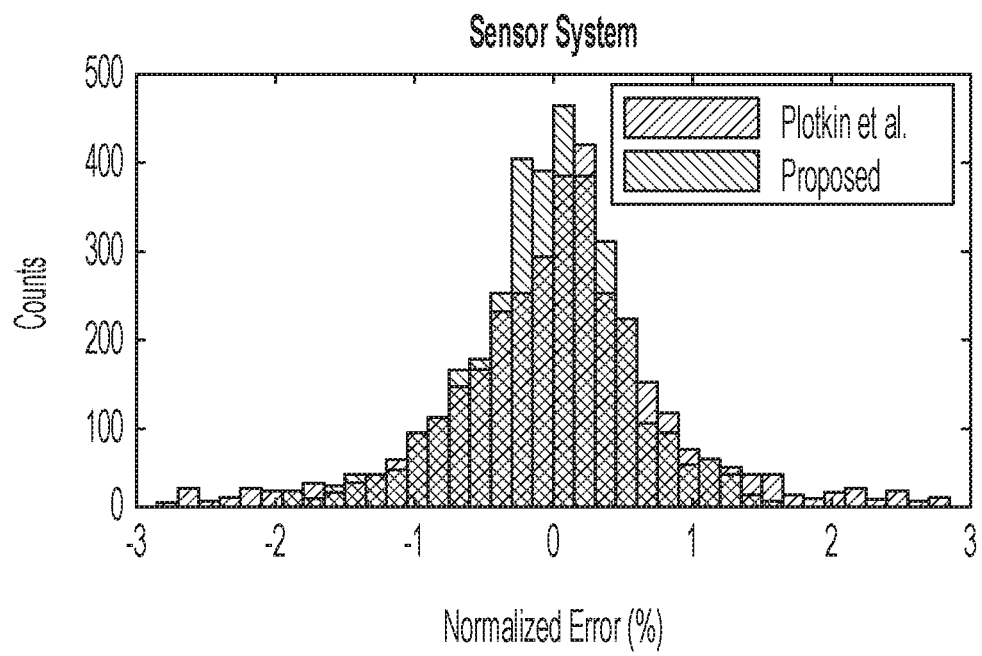
Figure 7B:
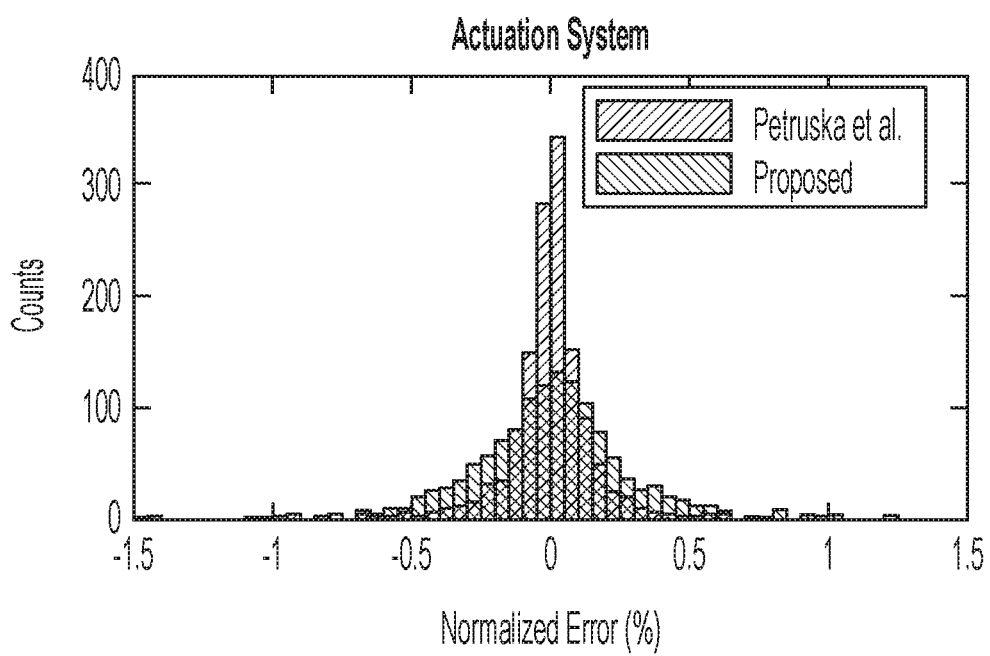

Further embodiments of the invention are described in the following description of the Figures. The invention will be explained in the following in detail by means of embodiments and with reference to the drawing in which is shown:

FIG. 1: an exemplary experimental setup for a sensing and actuating system;

FIG. 2: a table explaining the different parameters;

FIG. 3: an exemplary explanation of the geometric parameters of the sensing and actuating systems;

FIGS. 4A to 4F: exemplary simulation results for the experimental setup of FIG. 1, FIG. 5: a table showing a specification for a real application of a magnetic actuation and sensing system;

FIG. 6: a table showing the initial parameters and tolerances for the application of FIG. 5;

FIGS. 7A to 7B: experimental calibration results; and

FIGS. 8A to 8D: a comparison of the model fitting accuracy using different actuation models.

FIG. 1 shows the targeted calibration system 10, which is composed of a magnetic sensing system 12 with a plurality of magnetic sensors 14, a workspace 16 for the objects (or patients) to be measured (not shown) as well as a magnetic actuation system 18 with a plurality of magnetic actuators 20.

The magnetic sensing system 12 lies within its sensing system level 22 whereas the magnetic actuation system 18 lies within an actuation system level 24. Both levels 22, 24 are shown by an exemplary dashed line. The sensing system level 22 is spaced apart from the actuation system level 24, with the workspace being arranged between the two.

The magnetic actuators 20 are composed of electromagnets which each comprise a coil 26 and core 28. A respective current sensor (not shown) can be attached to the magnetic actuators 20.

The outputs of the plurality of magnetic actuators 20, the plurality of magnetic sensors 14 and the current sensors is made available at a common evaluation unit 30. The evaluation unit 30 is configured to simultaneously calibrate the magnetic actuators 20 and the magnetic sensors 14 using a calibration model.

The magnetic actuation and sensing system 10 can be calibrated simultaneously by generating a plurality of arbitrary magnetic fields at the workspace 16 by applying a plurality of electric currents at the magnetic actuators 20.

Each of the respectively generated magnetic fields is measured with the sensing system 12 in the workspace 16 and each respective electric current is measured with the current sensor at each of the magnetic actuators 20.

A magnetic field of a random known sample magnet (not shown) is also measured with the sensing system 12. For this the sample magnet is placed at an arbitrary position and orientation in the workspace 16.

The measured data is then fed into a calibration model, with the calibration model being based on a sensor measurement model in combination with a magnetic actuation model. Using the calibration model a solution of the model parameters is found via a numerical solver in order to calibrate both the actuation and sensing systems at the same time.

Thus, the uncalibrated sensors and electromagnets work as calibration sources. Although the parameters of the system are inaccurate prior to the calibration, all the parameters for the sensor and actuation systems are calibrated simultaneously by the property of the calibration model. For this it is assumed that the current sensors are pre-calibrated before the calibration and the positions of the magnetic sensors are known.

It should be noted that each of the plurality of generated magnetic fields is non-uniform throughout the workspace 16, which is generated from a solenoidal electromagnet.

It should further be noted that the calibration model may comprise a parameter set, which includes sensor parameters and actuator parameters, wherein the sensor parameters comprise parameters for position, orientation, axis distortion, axes distortion and gain of each sensor, and wherein the actuator parameters comprise parameters for position, orientation and magnetic moment of each actuator.

FIG. 2 shows a table explaining all the parameters which are necessary for the simultaneous calibration of the sensing and actuation system 10, which will be described later.

FIG. 3 shows a geometric description of some of the parameters used for calibration. All the position vectors and rotation matrices are expressed in a global frame $\{G\}$. The local frame $\{L\}$ is used to express gains of the sensors, $m_j$ and $m'_j$ show magnetic moments of j- and j'-th actuators 20, respectively. Black dots show the shifted center of the magnetic sources due to mutual inductions.

FIGS. 4A to 4F show simulation results from a simultaneous calibration, wherein FIGS. 4A and 4B show rendered images of configurations of the OctoMag- and a large-scale OctoMag-system. The hollow cylinders stand for the coils 28, whereas the inner cylinders stand for the cores 26. The sphere in the middle of the Figures shows an exemplary workspace 16, whereas the sensing system 12 is shown via a plate 12 below the workspace 16.

FIGS. 4C to 4D and FIGS. 4E to 4F show normalized error distributions of the sensing system and actuation system, respectively, after the calibration. The Figures show that the standard deviation (STD) of the normalized errors is less than 0.45% in all the cases. The sensing and the actuation systems' coefficients of determination ($R^2$ values) are over 99.88% in all the cases.

FIGS. 5 and 6 show further tables which reveal the parameters and tolerances of a real application of the simultaneous calibration of a sensing and actuation system.

FIGS. 7A and 7B show the experimental calibration results, wherein FIG. 7A shows the sensing system calibration result which resulted from using the method according to the invention in contrast to results from a known state of the art individual calibration of a sensing system. The state of the art method showed a $R^2$ value of 99.57% with 0.97% STD of the normalized error. The method according to the invention on the other hand shows a $R^2$ value of 99.84% with 0.59% STD of the normalized error.

In FIG. 7B one can see the result of an actuation system calibration by using the method according to invention in contrast to the result of a known state of the art individual calibration. The state of the art calibration shows a $R^2$ value of 99.91% with 0.19% STD of the normalized errors, while the method according to the invention shows a $R^2$ value of 99.45% with 0.47% STD of the normalized errors.

Figure 8A:
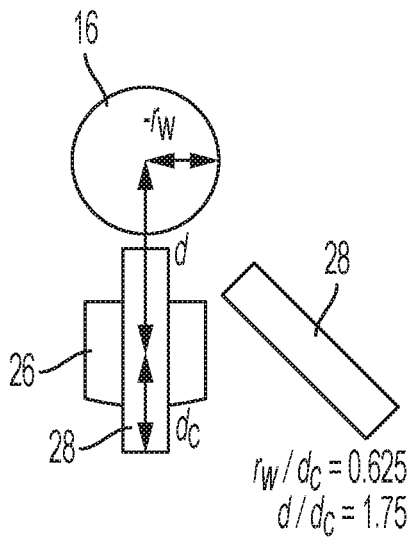
Figure 8C:
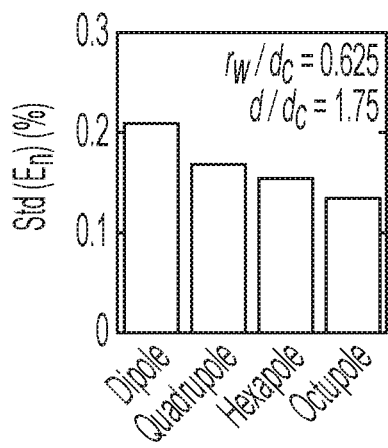
Figure 8D:
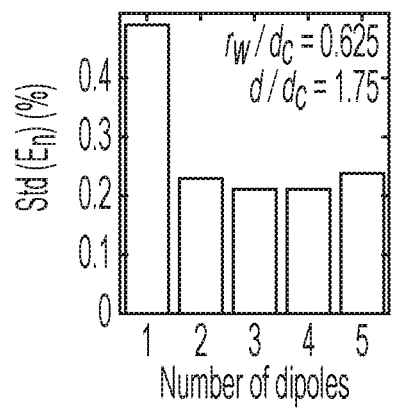
Figure 8B:
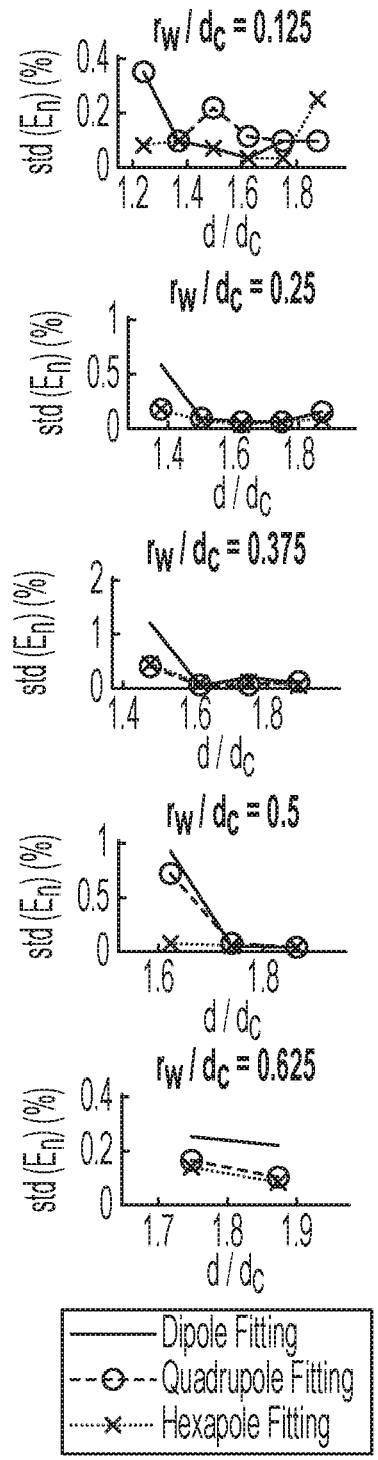

FIGS. 8A to 8B show a comparison of model fitting accuracy using different actuation models. In FIG. 8A, one can see an experimental setup, where a coil with a core and an extra core are used. The workspace 16 is shown by the sphere with a radius of $r_w$. The workspace 16 is placed above the closest coil 26 with a center-to-center distance d. The length of the cores 28 is $d_c$.

In this connection it should be noted that models to which the current invention is compared are respective models used for only calibrating either the sensors or the actuators, but neither are calibrated together at the same time using one model as is presently the case in the present invention.

FIG. 8B shows the actuation model fitting results using different orders of actuation models by varying the workspace's range and distance. For each workspace configuration, three dipoles, three dipoles with three quadrupoles and three dipoles with three quadrupoles and three hexapoles are used. The model actuation model fitting results using a dipole model together with up to different orders of multipole models and the results using different numbers of dipole sources are shown in the FIGS. 8C and 8D, respectively.

The simultaneous calibration method is described in more detail below on the basis of a specific example.

A. System Description

The targeted calibration system is composed of a plurality of magnetic sensors (sensor array) and a set of electromagnets. The final application of the system is to control a magnetic robot using the actuation system (electromagnets) while the magnetic robot is localized by a localization algorithm using sensor data.

The sensor array measures magnetic fields from a magnetic robot and the electromagnets. The magnetic sensor can be either mono-axial or multi-axial. In described example a triaxial sensor is used as that sensor is harder to calibrate. With the coupled magnetic fields from the magnetic robot and the actuators, the robot can be localized by a known algorithm.

The actuation system generates desired magnetic fields and their spatial gradients at the center of the magnetic robot. The magnetic field is non-uniform throughout the workspace. Systems using non-uniform magnetic fields from solenoidal electromagnets, such as OctoMag or MiniMag, could be categorized as an applicable system. The example system (FIG. 1) has 64 sensors and 9 electromagnets.

B. Framework: Calibration as Bundle Adjustment

Bundle adjustment (BA) has been employed in online simultaneous localization and mapping (SLAM) and offline structure from motion (SfM), which enables precise recovery of the parameters of both the sensors and landmarks. It is essentially an optimization-based method that can handle the simultaneous estimation of large numbers of parameters. It can be robust to external noises in the measurements. In the case where the measurement noise is zero-mean and normally distributed, BA solves a maximum likelihood estimation problem.

In the method according to the invention, the measurements of the electric currents and the magnetic field can be treated equivalently as the feature points of images in BA. The positions, orientations and gains of the actuators and sensors are similar to the parameters of landmarks and camera(s). These parameters are constrained by the magnetic field dipole model under specific conditions.

In order to solve the calibration problem in the BA framework, it must be considered parametrization, error modeling, building constraints, removing gauge freedom and choosing a proper optimization process.

C. Parametrization

The proposed method involves a large set of parameters (the example system in the experiment has 1836 parameters to be calibrated). In such a large parameter space, an appropriate parametrization is required for a reliable optimization result. The parameter set is composed of sensor parameters and actuator parameters. The systems of the parameters are represented in FIGS. 2 and 3.

1) Sensor Parameters: A sensor has parameters for position, orientation, axis distortion, axes distortion and gain (either linear or non-linear). For a general sensor calibration, each sensor is regarded as having a non-linear response and a cross-coupling effect among the axes. The non-linearity is attributed by hard-iron or soft-iron effect from ferrous material on the circuit board. The distortion of axes is attributed by fabrication errors from the manufacturing process or thermal stress from the soldering process. In the case of an extremely sensitive triaxial magnetometer, such as a fluxgate magnetometer, the transverse field effect (TFE) becomes an additional source for the non-linearity and cross-coupling effects.

A couple of models are presented to capture the non-linearity and the axes distortion. These models are for single triaxial magnetometers, so the axis rotation is neglected assuming that the axis rotation is pre-calibrated. However, in general, a system with multiple sensors might have a different orientation for each sensor. This is because the fabrication process might change the orientations or different orientations can be intended to increase the signal to noise ratio to a certain direction. Involving the non-linearity, cross-coupling and sensor rotation, a 3-D polynomial model could be used. The model can be easily expanded by increasing the order of the polynomials with the expense of computation.

In this example a 3-D quadratic model is used. This model is not only able to capture the non-linearity of the sensors precisely, but is also computationally practical. The 3-D quadratic model with sensor orientations involves 27 parameters for each sensor. It is assumed that the positions of the sensors are known. The experimental setup has 64 sensors, thus 1782 parameters for sensors are presented.

2) Actuator Parameters: A magnetic actuator has a position, an orientation and a magnetic moment. A typical electromagnet has a coil and core and their axes are aligned together. In such a case, the orientation and the magnitude of the magnetic moment of the electromagnet can be combined into a 3-D vector. A system with more than two cores has a mutual induction which might change the magnetic center's position and the magnetic moment's orientation compared to a single electromagnet presented. The experimental setup has 9 actuators, thus 54 parameters for the actuators presented.

D. Calibration Model

The calibration model is based on a sensor measurement model and magnetic actuation model. The magnetic fields from the actuators are measured by the magnetic sensors and the values are expressed in arbitrary units. Additionally, the electric currents are measured by the current sensors attached to the actuators. It is assumed that the current sensors are the only reliable sensors with zero-mean Gaussian noise corruption.

1) Sensor Measurement Model: The magnetic field is measured by the magnetic sensor array. A single sensor reads the magnetic flux density or the B-field through the voltage difference across the ends of a magneto-sensitive resistor. It is assumed that the sensor is non-linear, of which the axes are skewed and rotated, and the gains are different from the factory specifications. Using a quadratic model, the recovered B-field in the i-th sensor at the k-th measurement is $$\bar{b}_{ik}(p_{si}, v_{ik}) = G_i v_{ik} + \begin{bmatrix} v_{ik}^T H_{x,i} v_{ik} \\ v_{ik}^T H_{y,i} v_{ik} \\ v_{ik}^T H_{z,i} v_{ik} \end{bmatrix},$$

where $p_{s,i}$ is an array of parameters for $G_i$, $H_{y,i}$, and $H_{z,i}$. In this expression $G_i$, is a linear mapping with no additional constraints, meaning it represents the effects of scaling, rotation and shear. $H_{x,i}$, $H_{y,i}$, and $H_{z,i}$ are symmetric 3×3 matrices, which involve rotations and quadratic terms together. Note that the other symbols are explained in FIG. 2.

As each sensor in the sensor array has multiple measurements, it is convenient to express the recovered B-field values from the whole measurements in a stacked matrix form as $$\mathbb{V}_s(p_s, v) = \begin{bmatrix} \overline{b}_{11}(p_{s,1}, v_{11}) & \cdots & \overline{b}_{1L}(p_{s,1}, v_{1L}) \\ \vdots & \ddots & \vdots \\ \overline{b}_{N1}(p_{s,N}, v_{N1}) & \cdots & \overline{b}_{NL}(p_{s,N}, v_{NL}) \end{bmatrix},$$

where $p_s$ and $v$ are stacked vectors for all $p_{s,i}$ and $v_{ik}$, respectively.

2) B-field Actuation Model: The system described in FIG. 1 can be effectively modelled by the dipole magnetic field. This assumption is useful when a large-scale optimization is involved because the dipole model avoids intensive computations, but gives accurate estimation. Methods using the magnetic dipole model to fit the magnetic field for a workspace are already known. The known method uses a magnetic dipole to fit the magnetic field of a unit-current contribution. By increasing the number and the order of magnetic poles, more accurate model could be achieved. Due to the large search space in the optimization, it is preferable to have the least amount of parameters. In the current problem, a single dipole model for each unit-current contribution is chosen. A detailed analysis on the accuracy of the model with respect to the model complexity is present in the following.

The dipole magnetic field on the i-th sensor form the j-th actuator at the k-th measurement is expressed as $$b_{ij,k} = B_{ij} m_j I_{jk};$$

$$B_{ij} \equiv \frac{\mu_0}{4\pi \|r_{ij}\|^3}(3\hat{r}_{ij}\hat{r}_{ij}^T - \mathbb{1}), r_{ij} \equiv r_i - r_j,$$

where $b_{ij,k}$ is the magnetic field vector in $R^3$, $B_{ij}$ is a 3×3 matrix which only depends on the displacement vector $r_{ij}$, $\hat{\cdot}$ is a unit vector normalization operator, $\mathbb{1}$ is the identity matrix and $\mu_0$ is the permeability of free space.

For magnetically actuated robots, multi-degrees-of-freedom (DOF) actuation is preferred as it can give more authority to control the robot and avoid singularities or reduce the energy consumption using the redundancy. Because the magnetic field is superimposed at a point, it can be considered the sum of the magnetic fields from each actuator as the resultant magnetic field.

The magnetic field at multiple measurement points from multiple current inputs could be expressed in a matrix equation as $b_k = \mathbb{B} \, \mathbb{M} \, i_k$, where $$\mathbb{B} = \begin{bmatrix} B_{11} & \cdots & B_{1M} \\ \vdots & \ddots & \vdots \\ B_{N1} & \cdots & B_{NM} \end{bmatrix} \text{ and } \mathbb{M} = \begin{bmatrix} m_1 & \cdots & 0 \\ \vdots & \ddots & \vdots \\ 0 & \cdots & m_M \end{bmatrix},$$

$b_k$ is a modelled magnetic field on all the sensors in a stacked matrix form, $\mathbb{B}$ is the actuation matrix from magnetic moments to the magnetic field on each sensor, $\mathbb{M}$ is the magnetic moment package for the actuators (diagonal: magnetic moments, off-diagonal: zero-vectors) and $i_k$ is a measured electric current for all the actuators in a stacked form at the k-th measurement.

Similar to the sensor measurement model, it is convenient to express the B-field values into a stacked matrix form as $\mathbb{V}_a(p_a, i) = [b_1 \ldots b_L] = \mathbb{B} \, \mathbb{M} \, [i_1 \ldots i_L] = \mathbb{B} \, \mathbb{M} \, \mathbb{J}$, where $p_a$ is a vector including all the actuation parameters, $i$ is a stacked vector for all $i_k$ and $\mathbb{J}$ is a stacked matrix for all the current measurements.

E. Formulation of a Cost Function

The cost function can be formulated by minimizing the errors between the B-field values given by the sensor model and the actuation model. The problem can be stated in the least square manner, $$\underset{p_s, p_a}{\text{minimize}} \|\mathbb{V}_s(p_s, v) - \mathbb{V}_a(p_a, i)\|_F^2$$

$$\text{subject to } p_{s,lb} \preceq p_s \preceq p_{s,ub}$$
$$p_{a,lb} \preceq p_a \preceq p_{a,ub}$$
$$g(p_s) = 0$$

where $\|\cdot\|_F$ is the Frobenius norm, $p_s$ are sensor parameters, $p_{s,lb}$ and $p_{s,ub}$ are sensor parameters' lower and upper boundaries, respectively, $p_a$ are actuator parameters and $p_{a,lb}$ and $p_{a,up}$ are actuator parameters' lower and upper boundaries, respectively; $\preceq$ is an element-wise (general) inequality symbol. These boundaries come from the manufacturing tolerance or estimation tolerance for each parameter. $g(\cdot)$ is an additional constraint to resolve the gauge freedom, which is described in (8).

1) Minimum Number of Measurements: The total number of the equations should be larger than the total number of parameters to solve the optimization problem. The total number of the equations is a multiplication of the number of the sensor elements, 3N (in the case of a triaxial sensor), and the total number of measurements L. Additionally, there is an additional constraint for the optimization, $g(\cdot)$, which gives one more equation. The total number of parameters are the sum of the number of the sensor parameters, 27 N, and the number of actuator parameters, 6 M. This formulates an inequality, $3NL+1 \geq 27N+6M$, which results in $$L \geq 9 + \frac{6M - 1}{3N}.$$

Although the minimum number of the measurements is defined, it is beneficial to collect measurement data more than the minimum number to improve calibration accuracy. The large number of data minimizes Gaussian error from the sensor system effectively through the optimization process.

2) Resolving Gauge Freedom: There is a gauge freedom in the magnetic scale. The measurements are invariant under a scaling of either the norm of one of the $G_i$ values. To resolve the gauge freedom, a physical reference needs to be introduced, which can give an absolute value for the magnetic scale.

The physical reference is introduced using a permanent magnet whose magnetic moment is known. By measuring the magnetic field of the permanent magnet inside the workspace, the magnetic moments of the actuators and the gain for the sensors are related with the physical values.

A "temporary" value for the gauge freedom parameter would be needed for a better calibration. This is because the measurement of the magnetic field of the permanent magnet is not redundant as the measurement of the magnetic fields form the electromagnets (number of the sample is much smaller and the noise is not compensated). The temporary value can be corrected after the first calibration. Although the measurement of the magnetic field form the reference magnet is a one-time measurement, it is preferred to expose the sensors to the magnetic field of the magnet for a long period of time and take a mean value of the measured data. This proves would minimize the effect of Gaussian noise during the measurement of the reference magnet.

The temporary magnetic scale is added on the cost function. The magnetic scale can be fixed by constraining either the sensor gain or the magnetic moment of the actuator to a certain number. The sensor gain might be close to the real value as it is specified in the manufacturer's data sheet. Fixing the mean value of the gain of the sensors as the best pre-knowledge (magnetometer specification data) as $$\text{mean}\left(\frac{\|G_i\|_F^2}{3}\right) - g^2 = 0$$

where g is the gain value of the sensors in the specification sheet. Adding this to the constraint in the scalar function g(•) of (6) finalizes the formulation for the optimization task.

3) Reassignment of Global Reference: The gauge freedom is fixed to the "temporary" value in the previous section. The value should be corrected according to the absolute physical value. This procedure should be performed after the first main optimization task.

The reference reassignment proves involves additional optimization; however we use the result parameters from the first optimization. We can formulate the optimization task to find the magnetic scale of the system compared with the reference magnet. The optimization is formulated as $$\underset{\alpha, r_r, \hat{n}_r}{\text{minimize}} \|\alpha \nabla_s(p_s, v_r) - [B_{1r} \ldots B_{N_T}]^T \hat{n}_r m\|_2^2,$$

where α is the magnetic scale correction factor, $v_r$ is the magnetic field measurement data when the reference magnet is in the workspace, $B_{ir}$ is formulated using relative positions, $r_i$-$r_r$, $r_r$ is the position of the reference magnet, $\hat{n}_r$ is the orientation vector of the reference magnet and m is the known magnetic moment of the reference magnet.

Using α from the optimization, the magnetic scales can be assigned as $G^*_i = \alpha G_i$, $H^*_i = \alpha H_i$, $m^* = \alpha m$, where the '*' symbol means a corrected value.

F. Choosing a Numerical Solver

The interior-point algorithm (IPA) is chosen to solve the bundle adjustment problem. Because the non-linear optimization problem stated in (6) has both equality and inequality constraints and a high-dimensional parameter space to optimize over, an optimization solver is needed which can handle the constraints well.

Simulation Results

The proposed method was tested in a simulation environment, where all the system parameters are known as the ground-truth for the ease of comparison. As a general solenoid type magnetic actuation system, OctoMag and its large-scaled version is chosen as simulation models (configurations are shown in FIGS. 4A and 4B). Those systems are modelled in a commercialized finite-element-analysis (FEA) software (COMSOL™, Comsol group).

The sensor system was simulated based on the data sheet of the sensor for the experiments. The sensor array has sixteen sensors in 2-D grid and the sensor array was placed tangent to the workspace. The placement of the sensor array is to simulate a system which uses the sensor array as a localization system, where the sensor array does not disturb the movement of the magnetic robot, but close to sense the magnetic field from it.

Form the ground-truth configuration, random magnetic fields were generated with random electric current inputs. The random electric currents and magnetic fields were measured with virtual electric current sensors and magnetic sensors with Gaussian noises. The magnetic sensors have 900 nT standard deviation (STD) Gaussian noise, and the current sensors have 10 mA STD Gaussian noise. These measurements were fed into the optimization task. The parameter boundaries were 5% offset from the ground-truth values, except the magnetic moments as they are hard to predict before the calibration. From the given configuration, there were 675 parameters and 1 non-linear constraints in total. For the termination condition of the optimization, the first-order optimality tolerance was set to the noise level of the sensors.

The validation data set is generated separately to check the accuracy of the model. The actuation model validation set is the B-field set inside the workspace, when coils are running with arbitrary inputs. The sensing model validation set is the B-field set at the place of the sensor array with different current inputs tan training datasets.

FIGS. 4A-4F shows the simulation result. After the calibration, the sensor and actuation model had shown low normalized errors. STD of the normalized error of the sensing and actuation systems were 0.35%, 0.45% for Octo-Mag system, respectively, and 0.59% and 0.062% for the large-scale OctoMag system, respectively. The determinants of coefficient ($R^2$ value) for all cases were over 99.88%.

Experimental Results

A. Experimental setup and procedure: The proposed method was applied to a custom-designed magnetic localization and actuation system 10 (FIG. 1). The system consists of nine electromagnets 20 and sixty-four triaxial magnetic sensors 14 located on an 8×8 grid with 30 mm nodal distance. The sensor array was placed 250 mm above the central electromagnet in z-direction and their centers were aligned on the xy-plane. The system specifications are shown in FIG. 5.

Manufacturing errors are present in both the localization and actuation systems. The sensing system involves errors from the orientation and the sensitivity of each sensor. The electromagnet contains a position shift due to the mutual inductance, and a model error from the magnetic moment mapping. All of these design parameters and manufacturing tolerances are shown in FIG. 6. Note that the initial parameters define the initial conditions, and tolerances defines the boundary conditions for the numerical solver.

Before the calibration procedure, the DC magnetic field around the system and the current sensor offset are nullified. The sensor system's values are measured for a period of time (20 seconds) and their mean values are set as nullifying offsets. The magnetic field noise floor was 50 μT and current sensor offset was ±5 mA.

In the experiment, the electromagnet generated five-hundred random magnetic fields (L=500) from current inputs ranging in [−3,3] A. The currents were measured by the current sensors while the magnetic field was measured by each magnetic sensor independently. After the measurements, the magnetic field of the reference magnet was measured inside the workspace in an arbitrary orientation and position. All the measurement data were fed into (6) and the optimization task was solved by the interior-point algorithm. The data measurements and the optimization took three minutes and fifteen minutes, respectively. After the optimization, the parameters were recorrected to fix the gauge freedom using (9) and (10).

B. Magnetic Sensor System Calibration Result: The sensor measurement was compared with the ground-truth data. A triaxial Gauss meter was used for the ground-truth data measurement. To generate magnetic fields to be measure, a set of random current inputs ran in the coils. The random current inputs were generated using a uniform distribution within [−1, 1] A. The input currents should be within a proper range, such that the magnitude of the magnetic field is linear to the input currents and the magnetic field does not saturate the magnetic sensors. The magnetic field was measured first by the sensor array. After that, the Gauss meter measured the magnetic field at the same location of each sensor with the same current input. In total 1350 data points were measured for both the sensor array and the Gauss meter.

As a reference method, we applied the calibration method from Plotkin et al. to the sensor system calibration. The method uses a permanent magnet to calibrate a magnetic sensor system. The method is modified to calibrate triaxial magnetic sensors, whereas the original method is for single axis magnetic sensors. $\phi$ 6×6 mm$^3$ NdFeB N52 magnet was used as the calibration source. The magnet was placed in hundred different locations and its magnetic field was measured by the sensor array.

FIG. 7A shows the sensor system calibration result. Using the proposed method, the sensor model had $R^2$ value of 99.84% and the normalized STD of 0.59%. The calibration result from the reference method resulted in $R^2$ value of 99.57% and a normalized error STD of 0.97%. The result shows that the proposed method is comparable with the previous sensing system calibration method.

C. Actuation System Calibration Result: The actuation system was calibrated simultaneously by the proposed method. To validate the calibration results, the modelled magnetic field from (4) was compared with the measured magnetic field using the Gauss meter. The input currents for the electromagnet were generated randomly within [−1, 1] A using a uniform distribution. The errors where calculated by the difference between the measured magnetic field and the modelled magnetic field. The Gauss meter was placed in a 50×50×50 mm$^3$ cubic grid which fit into the workspace. In total 1350 data points were measured and compared.

The result of the proposed method is compared with the result from the method of Petruska et al. as a reference. To collect the data for the reference method, the Gauss meter measured B-field directly inside the workspace when each coil ran −3 A, 0 A and 3 A. These data were fit into spherical harmonics model with one B-coefficient for each magnetic source.

FIG. 7B shows the experimental results. The proposed method resulted in the actuation model with $R^2$ value of 99.45% and the normalized error STD of 0.47%. The known calibration method resulted in $R^2$ value of 99.91% and a normalized error STD of 0.19%. The result shows that the proposed method is comparable with the previous actuation system calibration method.

Discussion

A. Actuator model's complexity and accuracy: More complex models for actuators, such as multipole expansion models using spherical harmonics, could also be potentially used in the simultaneous calibration method. A magnetic dipole field model was used in this experiment because the model is computationally tractable and yields accurate results in the tested systems. For these systems, a more complex model may improve the actuator calibration accuracy but will increase the computational costs and may result in over-fitting.

The model fitting accuracy was compared when using different actuator models, in terms of the number and order of the magnetic poles by varying the size of the workspace and the distance from magnetic sources to the workspace. A set of control experiments was conducted in a simulated environment using finite-element-analysis (FEA). FIG. 8A shows the simulated configuration where a coil 26 with a core 28 is placed near to another core 28. The workspace 16 dimensions, the bounding sphere radius $r_w$ and the distance between the center of the coil 26 and the center of the workspace 16, d, were varied and the magnetic field data from FEA was obtained when a unit-current flows through the coil 26. The magnetic field data were fitted with actuation models using already known methods.

FIGS. 8A-D shows the result of the actuation model fitting. In FIG. 8B, the general trend shows all multi-pole models work better when increasing the distance between the workspace and the magnetic sources. With a fixed number of magnetic sources (three sources), even the dipole model yields an STD value less than 1% in all ranges. FIGS. 8C and 8D show the accuracy of the model when the size and position of the workspace is fixed ($r_w/d_c$=0.375 and $d/d_c$=1.75). In FIG. 8C, with a fixed number of sources (three sources), by increasing the order of the poles, the accuracy of the model is improved. In FIG. 8D, the actuation model improves with an increased number of sources. In all cases, the simplest model (with a single dipole) fits the B-field in the workspace less than 1% STD of the normalized errors.

B. Placement of sensor arrays: The sensor array placement might affect the accuracy of the calibration result. If the sensor is too far away from the workspace, the sensor array could not observe the magnetic field around the workspace. In such a case, the actuation model on the sensor array is accurate, but might not in the workspace. To achieve the best result, it is preferred to place the sensor array inside the workspace. Then the magnetic field observed in the sensor array closely matches with the magnetic field of the workspace.

The sensor array could be placed near by the workspace as well. This is important for the applications where it is hard to place the sensor array inside the workspace due to mechanical constraints. Additionally, a system needs to be automated and calibrated regularly would be one of the applications. In such a case, it is recommended to place the sensor array as close as possible to the workspace, so that the B-fields on the sensors are close to the B-field of the workspace. Note that the simulations and experiments were conducted to simulate those cases where the sensor array is near to the workspace.

C. Applications of the method: There are two major applications of the method according to the invention. First, the method could be employed for an automatic calibration with minimal human intervention. This would be beneficial for a system which needs recalibration often. For example, magnetic sensors require gain updated due to their time-variant soft-iron effect or a long-term gain-offset drift from the environmental change, such as the Earth's magnetic field change. Depending on the time scale of the gain change of the system or environment, the update can be scheduled regularly. A user could expose the reference magnet to the sensor system before the calibration, and the rest of the calibration could be done automatically.

Second, the proposed method allows the automatic calibration for reconfigurable magnetic sensing and actuation systems. The reconfiguration may be beneficial for improving dexterity, energy efficiency or avoiding singularities of an actuation system. Especially, the reconfiguration of the system would be critical in medical robotics, because a treatment of a patient might have a preferred direction. In the case of the reconfiguration, the parameter space could be minimized including only the actuation parameters enabling in-Situ calibration.

The invention claimed is:

1. A method of simultaneously calibrating magnetic actuation and sensing systems for a workspace, wherein the actuation system comprises a plurality of magnetic actuators and the sensing system comprises a plurality of magnetic sensors, the method further comprising the following steps:
   generating a plurality of arbitrary magnetic fields at the workspace by applying a plurality of electric currents to the magnetic actuators;
   measuring each magnetic field with the sensing system in the workspace and measuring each respective electric current with a current sensor;
   measuring a magnetic field of a random known sample magnet with the sensing system at an arbitrary position and orientation in the workspace; and
   feeding all the measured data into a calibration model, wherein the calibration model is based on a sensor measurement model and a magnetic actuation model, and finding a solution of the model parameters via a numerical solver in order to calibrate both the actuation and sensing systems at the same time.

2. The method in accordance with claim 1, wherein the actuation and sensing systems each comprise an actuation system level and a sensing system level, respectively, wherein the workspace is sandwiched in between the actuation system level and the sensing system level.

3. The method in accordance with claim 1, wherein the magnetic actuators comprise electromagnets.

4. The method in accordance with claim 1, wherein the magnetic sensors can be on of mono-axial, triaxial and multi-axial sensors.

5. The method in accordance with claim 1, wherein each of the plurality of generated magnetic fields comprises a non-uniform shape throughout the workspace.

6. The method in accordance with claim 5, wherein the non-uniform shape is generated from a solenoidal electromagnet.

7. The method in accordance with claim 1, wherein the calibration model comprises a parameter set, which includes sensor parameters and actuator parameters, wherein the sensor parameters comprise parameters for position, orientation, axis distortion, axes distortion and gain of each sensor, and wherein the actuator parameters comprise parameters for position, orientation and magnetic moment of each actuator.

8. The method in accordance with claim 1, wherein the sensor measurement model includes a measurement of each generated magnetic field according to $$\bar{b}_{ik}(p_{si}, v_{ik}) \propto G_i v_{ik} + \begin{bmatrix} v_{ik}^T H_{x,i} v_{ik} \\ v_{ik}^T H_{y,i} v_{ik} \\ v_{ik}^T H_{z,i} v_{ik} \end{bmatrix}, \quad (1)$$

wherein $p_{s,i}$ is an array of parameters for $G_i$, $H_{x,i}$, $H_{y,i}$ and $H_{z,i}$, and wherein $H_{x,i}$, $H_{y,i}$ and $H_{z,i}$ are symmetric 3×3 matrices which involve rotations and quadratic terms together, $G_i$ is a linear mapping which represents effects of scaling, rotation and shear, and $v_{ik}$ is the magnetic senor reading.

9. The method in accordance with claim 1, wherein recovered B-field values are expressed in a stacked matrix form as $$\bar{\mathbb{V}}_s(p_s, v) \propto \begin{bmatrix} \bar{b}_{11}(p_{s,1}, v_{11}) & \ldots & \bar{b}_{1L}(p_{s,1}, v_{1L}) \\ \vdots & \ddots & \vdots \\ \bar{b}_{N1}(p_{s,N}, v_{N1}) & \ldots & \bar{b}_{NL}(p_{s,N}, v_{NL}) \end{bmatrix}, \quad (2)$$

and wherein $p_s$ and $v$ are stacked vectors for all $p_{s,i}$ and $v_{ik}$, respectively.

10. The method in accordance with claim 1, wherein the magnetic actuation model is based on a dipole model, where a dipole magnetic field on the i-th sensor from the j-th actuator at the k-th measurement is expressed as $$b_{ij,k} \propto B_{ij} m_j I_{jk}; \quad B_{ij} \propto \frac{\mu_0}{4\pi \|r_{ij}\|^3}(3\hat{r}_{ij}\hat{r}_{ij}^T - \mathbb{I}), \quad r_{ij} \propto r_i - r_j \quad (3)$$

where $b_{ij,k}$ is a magnetic field vector, $B_{ij}$ is a 3×3 matrix which only depends on the displacement vector $r_{ij}$, $\mathbb{I}$ is the identity matrix and $\mu_0$ is the permeability of free space.

11. The method in accordance with claim 1, wherein the magnetic fields at multiple measurement points are expressed as $$b_k \propto \mathbb{B} \mathbb{M} i_k, \text{ where } \mathbb{B} \propto \begin{bmatrix} B_{11} & \ldots & B_{1M} \\ \vdots & \ddots & \vdots \\ B_{N1} & \ldots & B_{NM} \end{bmatrix}, \mathbb{M} \propto \begin{bmatrix} m_1 & \ldots & 0 \\ \vdots & \ddots & \vdots \\ 0 & \ldots & m_M \end{bmatrix}, \quad (4)$$

$b_k$ are modelled magnetic fields on all the sensors, $\mathbb{B}$ is an actuation matrix mapping magnetic moments to the magnetic field on each sensor, $\mathbb{M}$ is a magnetic moment package for the actuators and $i_k$ is a measured electric current for all the actuators in a stacked form at the k-th measurement.

12. The method in accordance with claim 1, wherein B-field values are expressed as a stacked matrix form as $$\mathbb{V}_a(p_a, i) \propto [b_1 \ldots b_L] \propto \mathbb{B} \mathbb{M} [i_1 \ldots i_L] \propto \mathbb{M} \mathbb{B} \mathbb{J} \quad (5)$$

where $p_a$ is a vector including all actuation parameters i is a stacked vector for all $i_k$, and $\mathbb{J}$ is a stacked matrix for all current measurements.

13. The method in accordance with claim 1, wherein the calibration model comprises a cost function which minimizes errors between the B-field values, wherein the cost function is formulated as $$\underset{p_s, p_a}{\text{minimize}} \|\mathbb{V}_s(p_s, v) - \mathbb{V}_a(p_a, i)\|_F^2 \quad (6)$$

subject to $\quad p_{s,lb} \leq p_s \leq p_{s,ub}$
$\quad\quad\quad\quad\quad p_{a,lb} \leq p_a \leq p_{a,ub}$
$\quad\quad\quad\quad\quad g(p_s) = 0,$ where $\|\cdot\|_F$ is the Frobenius norm, $p_s$ are sensor parameters $p_{s,lb}$ and $p_{s,ub}$ are sensor parameters' lower and upper boundaries, respectively, $p_a$ are actuator parameters, and $P_{a,lb}$ and $p_{a,up}$ are actuator parameters' lower and upper boundaries, respectively.

14. The method in accordance with claim 1, wherein a temporary magnetic scale is added to the calibration model which is derived from $$\text{mean}\left(\frac{\|G_i\|_F^2}{3}\right) - g^2 = 0, \quad (8)$$

where g is a gain value of the sensors.

15. The method in accordance with claim 1, wherein the calibration model comprises an optimization, which is formulated as $$\underset{\alpha,r_r,\hat{n}_r}{\text{minimize}} \|\alpha \overline{V}_s(p_s, v_r) - [B_{1r} \ldots B_{N_r}]^T \hat{n}_r m\|_2^2, \quad (9)$$

where $\alpha$ is a magnetic scale correction factor, $v_r$ is the magnetic field measurement data when the sample magnet is in the workspace level, $B_{ir}$ is formulated using relative positions $r_i$-$r_r$, $r_r$ is the position of the sample magnet, $\hat{n}_r$ is an orientation vector of the sample magnet and m is a known magnetic moment of the sample magnet.

16. A magnetic actuation and sensing system, comprising a plurality of magnetic actuators and a plurality of magnetic sensors, a respective output of the plurality of magnetic actuators and of the plurality of magnetic sensors being made available at a common evaluation unit, the evaluation unit simultaneously calibrating the magnetic actuators and the magnetic sensors in accordance with a method of claim 1 using a calibration model.

17. The magnetic actuation and sensing system according to claim 16, wherein the plurality of magnetic actuators comprises 3 to 25 magnetic actuators.

18. The magnetic actuation and sensing system according to claim 16, wherein the plurality of magnetic sensors comprises between 9 and 256 magnetic sensors.

19. The magnetic actuation and sensing system according to claim 16, wherein the number of magnetic sensor parameters and the number of magnetic actuator parameters are 27 N and 6 M, respectively, which formulates an inequality which, in the case of a triaxial sensor according to claim 4, can be expressed as 3NL+1≥27N+6M, which results in $$L \geq 9 + \frac{6M-1}{3N}. \quad (7),$$

where L represents a total number of measurements.

* * * * *